United States Patent
Lemke et al.

(10) Patent No.: US 7,022,286 B2
(45) Date of Patent: *Apr. 4, 2006

(54) FLUIDIC DEVICE FOR MEDICAL DIAGNOSTICS

(75) Inventors: John Lemke, Pleasanton, CA (US); Robert Justice Shartle, Livermore, CA (US); Victor Pan, Fremont, CA (US); Philip Cizdziel, San Jose, CA (US)

(73) Assignee: Lifescan, Inc., Milpitas, CA (US)

( * ) Notice: Subject to any disclaimer, the term of this patent is extended or adjusted under 35 U.S.C. 154(b) by 104 days.

This patent is subject to a terminal disclaimer.

(21) Appl. No.: 10/330,790

(22) Filed: Dec. 26, 2002

(65) Prior Publication Data

US 2003/0156984 A1 Aug. 21, 2003

Related U.S. Application Data

(63) Continuation of application No. 09/333,765, filed on Jun. 15, 1999, now Pat. No. 6,521,182

(60) Provisional application No. 60/093,421, filed on Jul. 20, 1998.

(51) Int. Cl.
*G01N 33/48* (2006.01)

(52) U.S. Cl. .................. 422/67; 422/68.1; 422/100; 422/103; 422/58; 422/61; 436/46; 436/164; 436/165; 356/39

(58) Field of Classification Search .............. 422/58, 422/61, 101, 62, 68.1, 67, 100, 103; 436/69–71, 436/164, 169, 177, 43, 46, 165; 356/39, 256, 356/427
See application file for complete search history.

(56) References Cited

U.S. PATENT DOCUMENTS

| | | | |
|---|---|---|---|
| 3,620,676 A | 11/1971 | Davis | |
| 3,640,267 A | * 2/1972 | Hurtig et al. | 600/578 |
| 4,088,448 A | 5/1978 | Lilja et al. | |

(Continued)

FOREIGN PATENT DOCUMENTS

| | | |
|---|---|---|
| EP | 0 803 288 | 10/1997 |
| EP | 0 974 840 A2 | 4/1999 |
| EP | 0 922 954 A2 | 6/1999 |
| EP | 1 069 427 A2 | 1/2001 |
| GB | 1526708 | 9/1978 |
| WO | WO 93/22452 | 11/1993 |
| WO | WO 94/02850 | 2/1994 |
| WO | WO 95/12117 | 5/1995 |
| WO | WO 99/18426 | 4/1999 |

OTHER PUBLICATIONS

Stimpson, Donald et al., "Parallel production of oligonucleotide arrays using membranes and reagent jet printing" Biotechniques, vol. 25, No. 5, Nov. 1998, pp. 886–890.
Stimpson, Donald et al. Biotechniques, vol. 25, No. 25, 1998, pp. 886–890.

*Primary Examiner*—Lyle A. Alexander
(74) *Attorney, Agent, or Firm*—Kagan Binder, PLLC (57) ABSTRACT

A fluidic medical diagnostic device permits measurement of analyte concentration or a property of a biological fluid, particularly the coagulation time of blood. The device has at one end a sample port for introducing a sample and at the other end a bladder for drawing the sample to a measurement area. A channel carries the sample from the sample port to the measurement area, and a stop junction, between the measurement area and bladder, halts the sample flow. The desired measurement can be made by placing the device into a meter which measures a physical property of the sample—typically, optical transmittance—after it has interacted with a reagent in the measurement area.

6 Claims, 11 Drawing Sheets

U.S. PATENT DOCUMENTS

| | | |
|---|---|---|
| 4,420,566 A | 12/1983 | Jessop et al. |
| 4,426,451 A | 1/1984 | Columbus |
| 4,756,884 A | 7/1988 | Hillman et al. |
| 4,761,381 A | 8/1988 | Blatt et al. |
| 4,822,568 A | 4/1989 | Tomita |
| 4,847,209 A | 7/1989 | Lewis et al. |
| 4,849,340 A | 7/1989 | Oberhardt |
| 4,868,129 A | 9/1989 | Gibbons et al. |
| 4,877,745 A | 10/1989 | Hayes et al. |
| 4,935,346 A | 6/1990 | Phillips et al. |
| 5,049,487 A | 9/1991 | Phillips et al. |
| 5,068,181 A | 11/1991 | Driscoll |
| 5,100,620 A | 3/1992 | Brenneman |
| 5,104,813 A | 4/1992 | Besemer et al. |
| 5,108,926 A | 4/1992 | Klebe |
| 5,208,163 A | 5/1993 | Charlton et al. |
| 5,230,866 A | 7/1993 | Shartle et al. |
| 5,242,606 A | 9/1993 | Braynin et al. |
| 5,338,688 A | 8/1994 | Deeg et al. |
| 5,366,902 A | 11/1994 | Cox et al. |
| 5,378,638 A | 1/1995 | Deeg et al. |
| 5,472,603 A | 12/1995 | Schembri |
| 5,504,011 A | 4/1996 | Gavin et al. |
| 5,508,521 A | 4/1996 | Kraft et al. |
| 5,591,403 A | 1/1997 | Gavin et al. |
| 5,610,287 A | 3/1997 | Nikiforov et al. |
| 5,627,041 A | 5/1997 | Shartle |
| 5,628,961 A | 5/1997 | Davis et al. |
| 5,674,699 A | 10/1997 | Saunders et al. |
| 5,677,195 A | 10/1997 | Winkler et al. |
| 5,700,695 A | 12/1997 | Yassinzadeh et al. |
| 5,708,278 A | 1/1998 | Lowne |
| 5,728,352 A | 3/1998 | Poto et al. |
| 5,736,404 A | 4/1998 | Yassinzadeh et al. |
| 5,827,681 A | 10/1998 | Krug et al. |
| 6,001,307 A | 12/1999 | Naka et al. |
| 6,033,866 A | 3/2000 | Guo et al. |
| 6,066,448 A | 5/2000 | Wohlstadter et al. |
| 6,066,504 A | 5/2000 | Jina |
| 6,084,660 A | 7/2000 | Shartle |
| 6,103,196 A | 8/2000 | Yassinzadeh et al. |
| 6,180,062 B1 | 1/2001 | Naka et al. |
| 6,261,519 B1 | 7/2001 | Harding et al. |
| 6,362,890 B1 | 3/2002 | Petrich et al. |
| 6,521,182 B1 | 2/2003 | Shartle et al. |
| 2002/0064480 A1 | 5/2002 | Shartie |
| 2002/0098114 A1 | 7/2002 | Harding et al. |
| 2002/0110486 A1 | 8/2002 | Shartie et al. |
| 2003/031594 A1 | 2/2003 | Shartie et al. |
| 2003/0156983 A1 | 8/2003 | Shartie et al. |
| 2003/0156984 A1 | 8/2003 | Lemke et al. |
| 2003/0210287 A1 | 11/2003 | Harding et al. |

\* cited by examiner

FLUIDIC DEVICE FOR MEDICAL DIAGNOSTICS

CROSS-REFERENCE

This application is a continuation of U.S. patent application Ser. No. 09/333,765, filed Jun. 15, 1999, now U.S. Pat. No. 6,521,182 which claims benefit from U.S. Provisional Patent Application Ser. No. 60/093,421, filed Jul. 20, 1998, which applications are incorporated herein by reference in their entirety.

BACKGROUND OF THE INVENTION

1. Field of the Invention

This invention relates to a fluidic medical diagnostic device for measuring the concentration of an analyte in or a property of a biological fluid.

2. Description of the Related Art

A variety of medical diagnostic procedures involve tests on biological fluids, such as blood, urine, or saliva, and are based on a change in a physical characteristic of such a fluid or an element of the fluid, such as blood serum. The characteristic can be an electrical, magnetic, fluidic, or optical property. When an optical property is monitored, these procedures may make use of a transparent or translucent device to contain the biological fluid and a reagent. A change in light absorption of the fluid can be related to an analyte concentration in, or property of, the fluid. Typically, a light source is located adjacent to one surface of the device and a detector is adjacent to the opposite surface. The detector measures light transmitted through a fluid sample. Alternatively, the light source and detector can be on the same side of the device, in which case the detector measures light scattered and/or reflected by the sample. Finally, a reflector may be located at or adjacent to the opposite surface. A device of this latter type, in which light is first transmitted through the sample area, then reflected through a second time, is called a "transflectance" device. References to "light" throughout this specification and the appended claims should be understood to include the infrared and ultraviolet spectra, as well as the visible. References to "absorption" are meant to refer to the reduction in intensity as a light beam passes through a medium; thus, it encompasses both "true" absorption and scattering.

An example of a transparent test device is described in Wells et al. WO94/02850, published on Feb. 3, 1994. Their device comprises a sealed housing, which is transparent or translucent, impervious, and rigid or semi-rigid. An assay material is contained within the housing, together with one or more assay reagents at predetermined sites. The housing is opened and the sample introduced just before conducting the assay. The combination of assay reagents and analyte in the sample results in a change in optical properties, such as color, of selected reagents at the end of the assay. The results can be read visually or with an optical instrument.

U.S. Pat. No. 3,620,676, issued on Nov. 16, 1971 to Davis, discloses a colorimetric indicator for liquids. The indicator includes a "half-bulb cavity", which is compressible. The bulb is compressed and released to form a suction that draws fluid from a source, through a half-tubular cavity that has an indicator imprinted on its wall. The only controls on fluid flow into the indicator are how much the bulb is compressed and how long the indicator inlet is immersed in the source, while the bulb is released.

U.S. Pat. No. 3,640,267, issued on Feb. 8, 1972 to Hurtig et al., discloses a container for collecting is samples of body fluid that includes a chamber that has resilient, collapsible walls. The walls are squeezed before the container inlet is placed into the fluid being collected. When released, the walls are restored to their uncollapsed condition, drawing fluid into and through the inlet. As with the Davis device, discussed above, control of fluid flow into the indicator is very limited.

U.S. Pat. No. 4,088,448, issued on May 9, 1978 to Lilja et al., discloses a cuvette, which permits optical analysis of a sample mixed with a reagent. The reagent is coated on the walls of a cavity, which is then filled with a liquid sample. The sample mixes with the reagent to cause an optically-detectable change.

A number of patents, discussed below, disclose devices for diluting and/or analyzing biological fluid samples. These devices include valve-like designs to control the flow of the sample.

U.S. Pat. No. 4,426,451, issued on Jan. 17, 1984 to Columbus, discloses a multi-zone fluidic device that has pressure-actuatable means for controlling the flow of fluid between the zones. His device makes use of pressure balances on a liquid meniscus at the interface between a first zone and a second zone that has a different cross section. When both the first and second zones are at atmospheric pressure, surface tension creates a back pressure that stops the liquid meniscus from proceeding from the first zone to the second. The configuration of this interface or "stop junction" is such that the liquid flows into the second zone only upon application of an externally generated pressure to the liquid in the first zone that is sufficient to push the meniscus into the second zone.

U.S. Pat. No. 4,868,129, issued on Sep. 19, 1989 to Gibbons et al., discloses that the back pressure in a stop junction can be overcome by hydrostatic pressure on the liquid in the first zone, for example by having a column of fluid in the first zone.

U.S. Pat. No. 5,230,866, issued on Jul. 27, 1993 to Shartle et al., discloses a fluidic device with multiple stop junctions in which the surface tension-induced back pressure at the stop junction is augmented; for example, by trapping and compressing gas in the second zone. The compressed gas can then be vented before applying additional hydrostatic pressure to the first zone to cause fluid to flow into the second zone. By varying the back pressure of multiple stop junctions in parallel, "rupture junctions" can be formed, having lower maximum back pressure.

U.S. Pat. No. 5,472,603, issued on Dec. 5, 1995 to Schembri (see also U.S. Pat. No. 5,627,041), discloses using centrifugal force to overcome the back pressure in a stop junction. When flow stops, the first zone is at atmospheric pressure plus a centrifugally generated pressure that is less than the pressure required to overcome the back pressure. The second zone is at atmospheric pressure. To resume flow, additional centrifugal pressure is applied to the first zone, overcoming the meniscus back pressure. The second zone remains at atmospheric pressure.

European Patent Application EP 0 803 288, of Naka et al., published on Oct. 29, 1997, discloses a device and method for analyzing a sample that includes drawing the sample into the device by suction, then reacting the sample with a reagent in an analytical section. Analysis is done by optical or electrochemical means. In alternate embodiments, there are multiple analytical sections and/or a bypass channel. The flow among these sections is balanced without using stop junctions.

U.S. Pat. No. 5,700,695, issued on Dec. 23, 1997 to Yassinzadeh et al., discloses an apparatus for collecting and manipulating a biological fluid that uses a "thermal pressure chamber" to provide the driving force for moving the sample through the apparatus.

U.S. Pat. No. 5,736,404, issued on Apr. 7, 1998, to Yassinzadeh et al., discloses a method for determining the coagulation time of a blood sample that involves causing an end of the sample to oscillate within a passageway. The oscillating motion is caused by alternately increasing and decreasing the pressure on the sample.

SUMMARY OF THE INVENTION

The present invention provides a fluidic diagnostic device for measuring an analyte concentration or property of a biological fluid. The device comprises a first layer and second layer at least one of which has a resilient region over at least part of its area, separated by an intermediate layer, in which cutouts in the intermediate layer form, with the first and second layers, a) a sample port for introducing a sample of the biological fluid into the device;

b) a first measurement area, in which a physical parameter of the sample is measured and related to the analyte concentration or property of the fluid;

c) a first channel, having a first end and a second end, to provide a fluidic path from the sample port at the first end through the first measurement area;

d) a first bladder at the second end of the first channel, comprising at least a part of the resilient region in at least the first or second layer and having a volume that is at least about equal to the combined volume of the first measurement area and first channel; and e) a first stop junction in the first channel between the first measurement area and first bladder that comprises a co-aligned through hole in at least the first or second layer, the through hole being overlaid with a third layer.

In another embodiment, the device comprises a first layer, which has a resilient region over at least a part of its area, and a second layer, separated by an intermediate layer, in which recesses in a first surface of the intermediate layer form, with the first layer, a) a sample port for introducing a sample of the biological fluid into the device;

b) a measurement area, in which the sample undergoes a change in a physical parameter that is measured and related to the analyte concentration or property of the fluid;

c) a channel, having a first end and a second end, to provide a fluidic path from the sample port at the first end through the measurement area; and d) a bladder, at the second end of the channel, comprising at least a part of the resilient region in the first layer and having a volume that is at least about equal to the combined volume of the measurement area and channel; and a stop junction in the channel between the measurement area and bladder that comprises two passages substantially normal to the first surface of the intermediate layer, each passage having a first end in fluid communication with the channel and a second end in fluid communication with a recess in a second surface of the intermediate layer, which recess provides fluid communication between the second ends of the passages.

The device is particularly well adapted for measuring prothrombin time (PT time), with the biological fluid being whole blood and the measurement area having a composition that catalyzes the blood clotting cascade.

DETAILED DESCRIPTION OF THE INVENTION

This invention relates to a fluidic device for analyzing biological fluid. The device is of the type that relates a physical parameter of the fluid, or an element of the fluid, to an analyte concentration in the fluid or to a property of the fluid. Although a variety of physical parameters—e.g., electrical, magnetic, fluidic, or optical—can form the basis for the measurement, a change in optical parameters is a preferred basis, and the details that follow refer to an optical device. The device includes a sample application area; a bladder, to create a suction force to draw the sample into the device; a measurement area, in which the sample may undergo a change in an optical parameter, such as light scattering; and a stop junction to precisely stop flow after filling the measurement area.

Preferably, the device is substantially transparent over the measurement area, so that the area can be illuminated by a light source on one side and the transmitted light measured on the opposite side. The measurement on the sample may be of a parameter that is not changing, but typically the sample undergoes a change in the measurement area, and the change in transmitted light is a measure of the analyte or fluid property of interest. Alternatively, light that is scattered from a fluid sample or light that passes through the sample and is reflected back through a second time (by a reflector on that opposite side) can be detected by a detector on the same side as the light source.

This type of device is suitable for a variety of analytical tests of biological fluids, such as determining biochemical or hematological characteristics, or measuring the concentration in such fluids of proteins, hormones, carbohydrates, lipids, drugs, toxins, gases, electrolytes, etc. The procedures for performing these tests have been described in the literature. Among the tests, and where they are described, are the following:
(1) Chromogenic Factor XIIa Assay (and other clotting factors as well): Rand, M. D. et al., Blood, 88, 3432 (1996).
(2) Factor X Assay: Bick, R. L. Disorders of Thrombosis and Hemostasis: Clinical and Laboratory Practice. Chicago, ASCP Press, 1992.
(3) DRVVT (Dilute Russells Viper Venom Test): Exner, T. et al., Blood Coag. Fibrinol., 1, 259 (1990).
(4) Immunonephelometric and Immunoturbidimetric Assays for Proteins: Whicher, J. T., CRC Crit. Rev. Clin Lab Sci. 18:213 (1983).
(5) TPA Assay: Mann, K. G., et al., Blood, 76, 755, (1990).; and Hartshorn, J. N. et al., Blood, 78, 833 (1991).
(6) APTT (Activated Partial Thromboplastin Time Assay): Proctor, R. R. and Rapaport, S. I. Amer. J. Clin. Path, 36, 212 (1961); Brandt, J. T. and Triplett, D. A. Amer. J. Clin. Path., 76, 530 (1981); and Kelsey, P. R. Thromb. Haemost. 52, 172 (1984).
(7) HbA1c Assay (Glycosylated Hemoglobin Assay): Nicol, D. J. et al., Clin. Chem. 29, 1694 (1983).
(8) Total Hemoglobin: Schneck et al., Clinical Chem., 32/33, 526 (1986); and U.S. Pat. No. 4,088,448.
(9) Factor Xa: Vinazzer, H., Proc. Symp. Dtsch. Ges. Klin. Chem., 203 (1977), ed. By Witt, I
(10) Colorimetric Assay for Nitric Oxide: Schmidt, H. H., et al., Biochemica, 2, 22 (1995).

The present device is particularly well suited for measuring blood-clotting time—"prothrombin time" or "PT time"—and details regarding such a device appear below. The modifications needed to adapt the device for applications such as those listed above require no more than routine experimentation.

Figure 1:
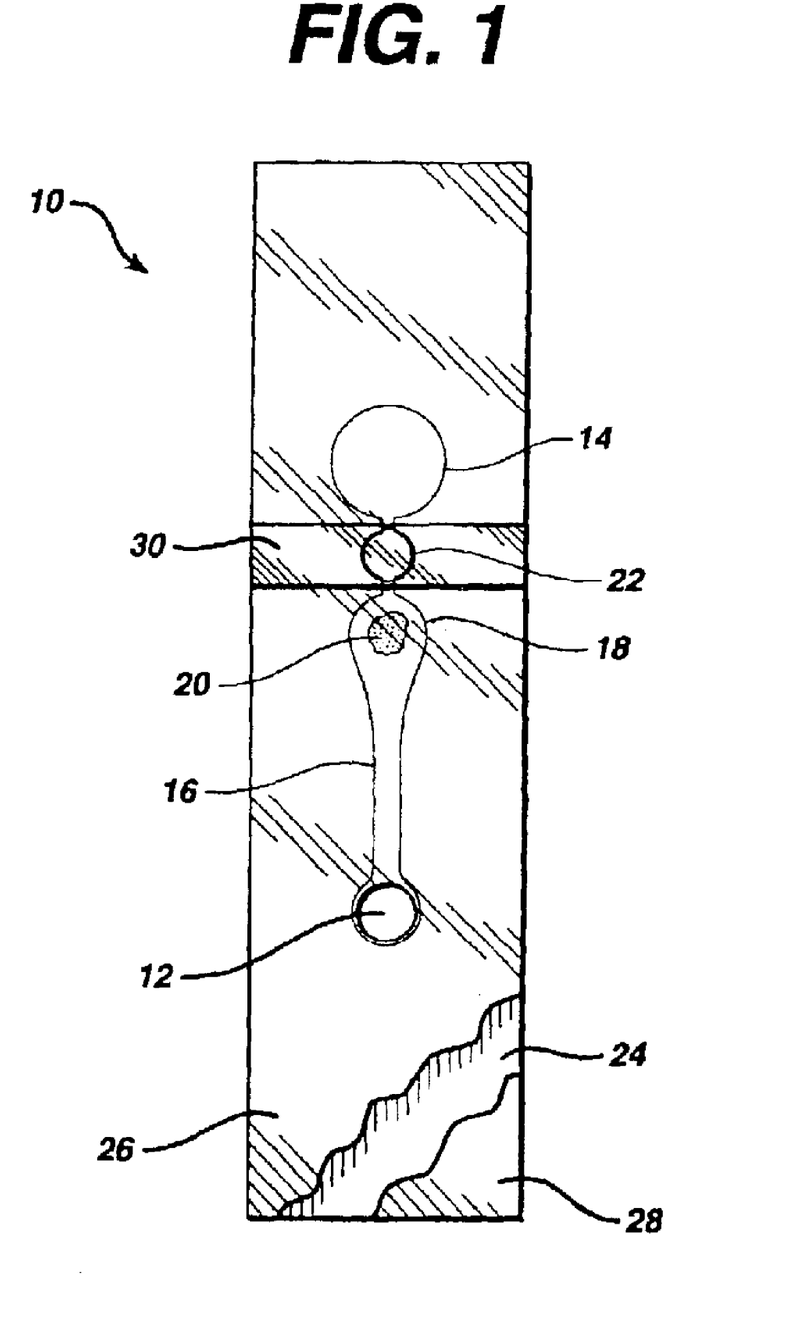
FIG. 1 is a plan view of a device of the present invention.
Figure 2:
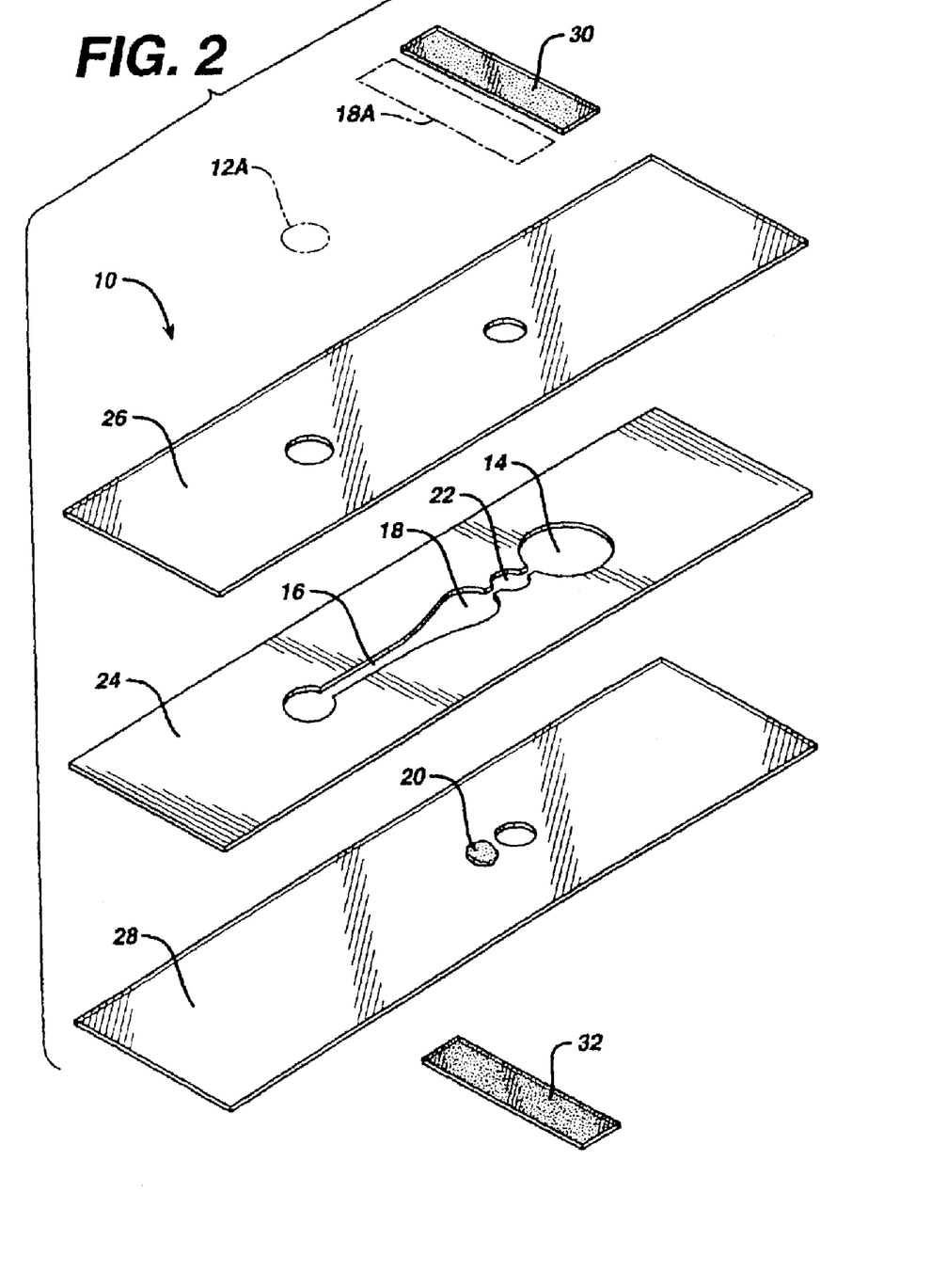
FIG. 2 is an exploded view of the device of FIG. 1.

FIG. 1 is a plan view of a device 10 of the present invention. FIG. 2 is an exploded view and FIG. 3 a perspective view of the device. Sample is applied to sample port 12 after bladder 14 has been compressed. Clearly, the region of layer 26 and/or layer 28 that adjoins the cutout for bladder 14 must be resilient, to permit bladder 14 to be compressed. Polyester of about 0.1 mm thickness has suitable resilience and springiness. Preferably, top layer 26 has a thickness of about 0.125 mm, bottom layer 28 about 0.100 mm. When the bladder is released, suction draws sample through channel 16 to measurement area 18, which preferably contains a reagent 20. In order to ensure that measurement area 18 can be filled with sample, the volume of bladder 14 is preferably at least about equal to the combined volume of channel 16 and measurement area 18. If measurement area 18 is to be illuminated from below, layer 28 must be transparent where it adjoins measurement area 18. For a PT test, reagent 20 contains thromboplastin that is free of bulking reagents normally found in lyophilized reagents.

Figure 3:
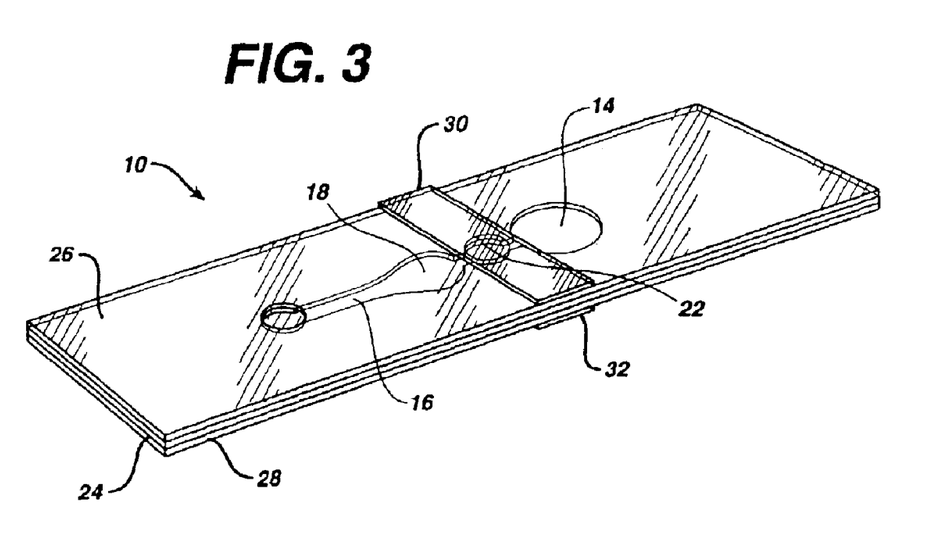
FIG. 3 is a perspective view of the device of FIG. 1.

As shown in FIGS. 1, 2, and 3, stop junction 22 adjoins bladder 14 and measurement area 18; however, a continuation of channel 16 may be on either or both sides of stop junction 22, separating the stop junction from measurement area 18 and/or bladder 14. When the sample reaches stop junction 22, sample flow stops. For PT measurements, it is important to stop the flow of sample as it reaches that point to permit reproducible "rouleaux formation"—the stacking of red blood cells—which is an important step in monitoring blood clotting using the present invention. The principle of operation of stop junctions is described in U.S. Pat. No. 5,230,866, incorporated herein by reference.

As shown in FIG. 2, all the above elements are formed by cutouts in intermediate layer 24, sandwiched between top layer 26 and bottom layer 28. Preferably, layer 24 is double-sided adhesive tape. Stop junction 22 is formed by an additional cutout in layer 26 and/or 28, aligned with the cutout in layer 24 and sealed with sealing layer 30 and/or 32. Preferably, as shown, the stop junction comprises cutouts in both layers 26 and 28, with sealing layers 30 and 32. Each cutout for stop junction 22 is at least as wide as channel 16. Also shown in FIG. 2 is an optional filter 12A to cover sample port 12. The filter may separate out red blood cells from a whole blood sample and/or may contain a reagent to interact with the blood to provide additional information. A suitable filter comprises an anisotropic membrane, preferably a polysulfone membrane of the type available from Spectral Diagnostics, Inc., Toronto, Canada. Optional reflector 18A may be on, or adjacent to, a surface of layer 26 and positioned over measurement area 18. If the reflector is present, the device becomes a transflectance device.

Figure 4:
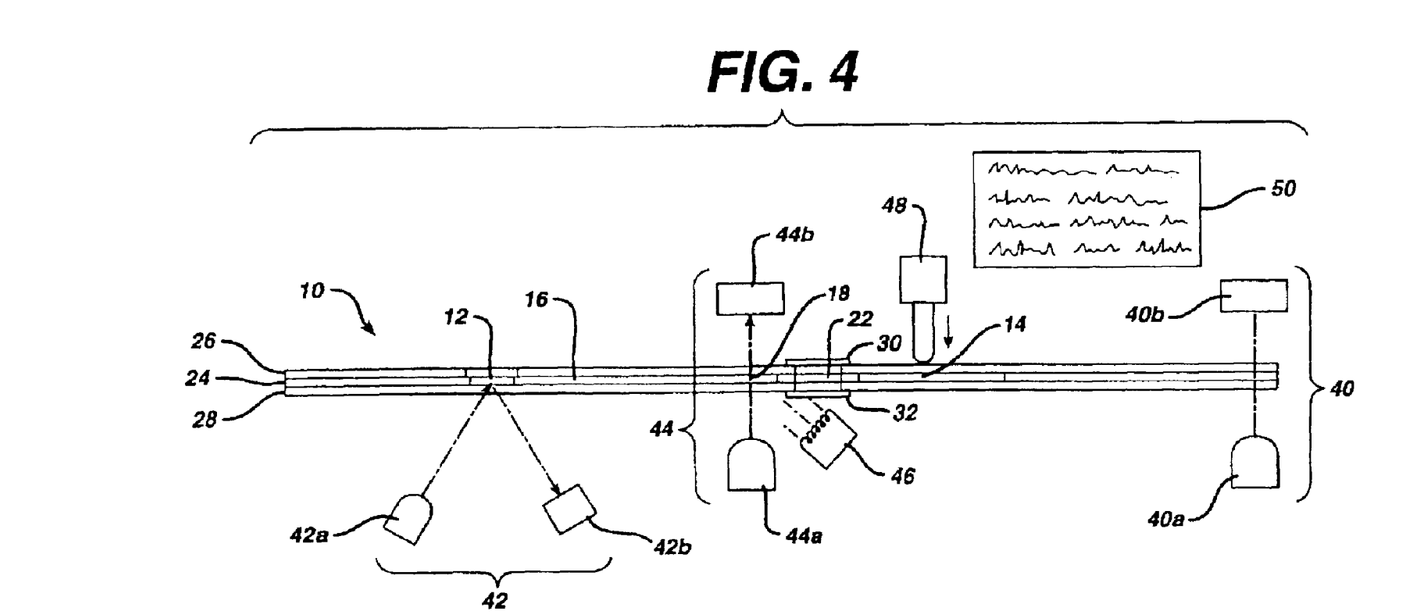
FIG. 4 is a schematic of a meter for use with a device of this invention.

The method of using the strip of FIGS. 1, 2, and 3 can be understood with reference to a schematic of the elements of a meter shown in FIG. 4, which contemplates an automated meter. Alternatively, manual operation is also possible. (In that case, bladder 14 is manually depressed before sample is applied to sample port 12, is then released.) The first step the user performs is to turn on the meter, thereby energizing strip detector 40, sample detector 42, measurement system 44, and optional heater 46. The second step is to insert the strip. Preferably, the strip is not transparent over at least a part of its area, so that an inserted strip will block the illumination by LED 40a of detector 40b. (More preferably, the intermediate layer is formed of a nontransparent material, so that background light does not enter measurement system 44.) Detector 40b thereby senses that a strip has been inserted and triggers bladder actuator 48 to compress bladder 14. A meter display 50 then directs the user to apply a sample to sample port 12 as the third and last step the user must perform to initiate the measurement sequence. The empty sample port is reflective. When a sample is introduced into the sample port, it absorbs light from LED 42a and thereby reduces the light that is reflected to detector 42b. That reduction in light, in turn, signals actuator 48 to release bladder 14. The resultant suction in channel 16 draws sample through measurement area 18 to stop junction 22. Light from LED 44a passes through measurement area 18, and detector 44b monitors the light transmitted through the sample as it is clotting. When there are multiple measurement areas, measurement system 44 includes an LED/detector pair (like 44a and 44b) for each measurement area. Analysis of the transmitted light as a function of time (as described below) permits a calculation of the PT time, which is displayed on the meter display 50. Preferably, sample temperature is maintained at about 37° C. by heater 46.

Figure 4A:
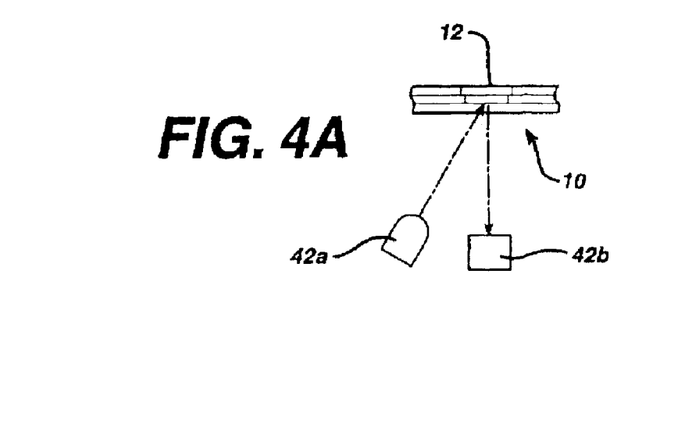
FIG. 4A depicts an alternative embodiment of an element of the meter of FIG. 4.
Figure 5:
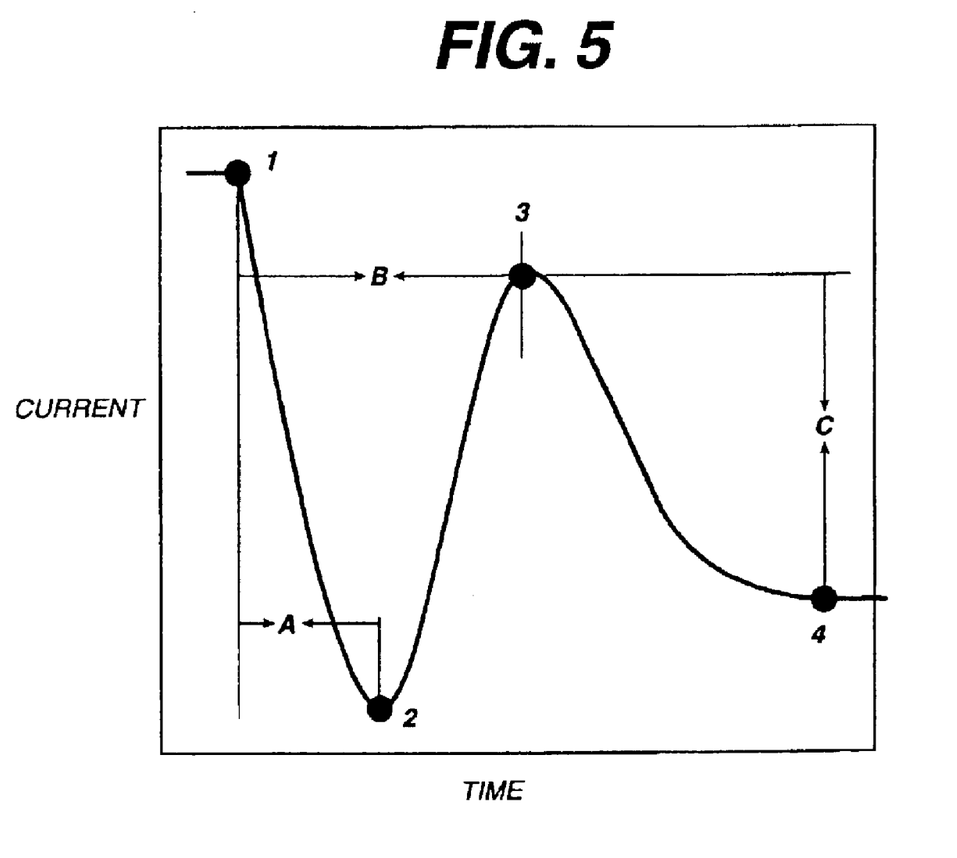
FIG. 5 is a graph of data that is used to determine PT time.

As described above, the detector senses a sample in sample port 12, simply by detecting a reduction in (specular) reflection of a light signal that is emitted by 42a and detected by 42b. However, that simple system cannot easily distinguish between a whole blood sample and some other liquid (e.g., blood serum) placed in the sample port in error or, even, an object (e.g., a finger) that can approach sample port 12 and cause the system to erroneously conclude that a proper sample has been applied. To avoid this type of error, another embodiment measures diffuse reflection from the sample port. This embodiment appears in FIG. 4A, which shows detector 42b positioned normal to the plane of strip 10. With the arrangement shown in FIG. 4A, if a whole blood sample has been applied to sample port 12, the signal detected by 42b increases abruptly, because of scattering in the blood sample, then decreases, because of rouleaux formation (discussed below). The detector system 42 is thus programmed to require that type of signal before causing actuator 48 to release bladder 14 The delay of several seconds in releasing bladder 14 does not substantially affect the readings described below FIG. 5 depicts a typical "clot signature" curve in which the current from detector 44b is plotted as a function of time. Blood is first detected in the measurement area by 44b at time 1. In the time interval A, between points 1 and 2, the blood fills the measurement area. The reduction in current during that time interval is due to light scattered by red cells and is thus an approximate measure of the hematocrit. At point 2, sample has filled the measurement area and is at rest, its movement having been stopped by the stop junction. The red cells begin to stack up like coins (rouleaux formation). The rouleaux effect allows increasing light transmission through the sample (and less scattering) in the time interval between points 2 and 3. At point 3, clot formation ends rouleaux formation and transmission through the sample reaches a maximum The PT time can be calculated from the interval B between points 1 and 3 or between 2 and 3. Thereafter, blood changes state from liquid to a semi-solid gel, with a corresponding reduction in light transmission. The reduction in current C between the maximum 3 and endpoint 4 correlates with fibrinogen in the sample.

The device pictured in FIG. 2 and described above is preferably formed by laminating thermoplastic sheets 26 and 28 to a thermoplastic intermediate layer 24 that has adhesive on both of its surfaces. The cutouts that form the elements shown in FIG. 1 may be formed, for example, by laser- or die-cutting of layers 24, 26, and 28. Alternatively, the device can be formed of molded plastic. Preferably, the surface of sheet 28 is hydrophilic. (Film 9962, available from 3M, St. Paul, Minn.) However, the surfaces do not need to be hydrophilic, because the sample fluid will fill the device without capillary forces. Thus, sheets 26 and 28 may be untreated polyester or other thermoplastic sheet, well known in the art. Similarly, since gravity is not involved in filling, the device can be used in any orientation. Unlike capillary fill devices that have vent holes through which sample could leak, the present device vents through the sample port before sample is applied, which means that the part of the strip that is first inserted into the meter is without an opening, reducing the risk of contamination.

Figure 6:
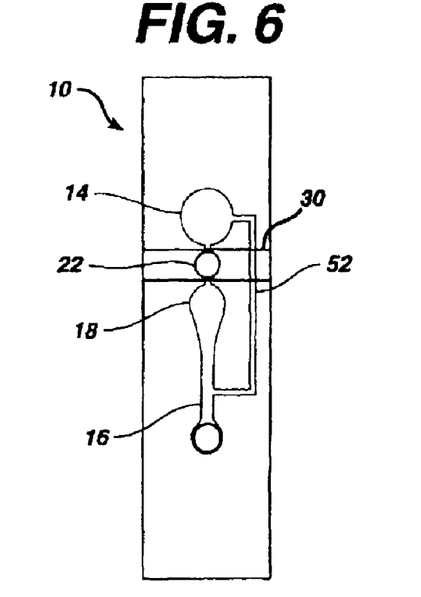
FIG. 6 is a plan view of an alternative embodiment of a device of this invention.

FIG. 6 is a plan view of another embodiment of the device of the present invention, in which the device includes a bypass channel 52 that connects channel 16 with bladder 14. The function and operation of the bypass channel can be understood by referring to FIGS. 6A, 6B, and 6C which depict a time sequence during which a sample is drawn into device 10 for the measurement.

Figure 6A:
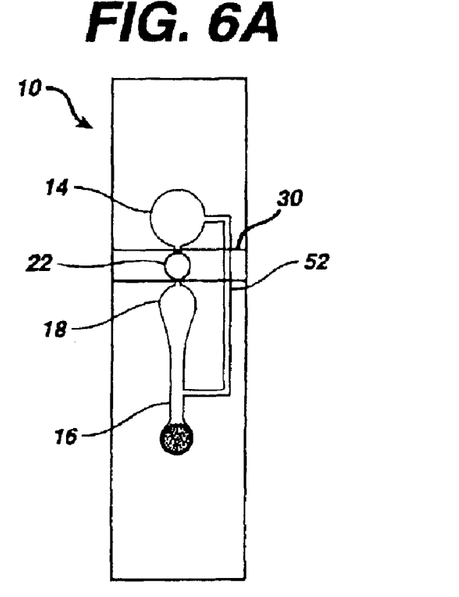
FIGS. 6A, 6B, and 6C depict a time sequence during which a sample is admitted to the device of FIG. 6.

FIG. 6A depicts the situation after a user has applied a sample to the strip, while bladder 14 is compressed. This can be accomplished by applying one or more drops of blood.

Figure 6B:
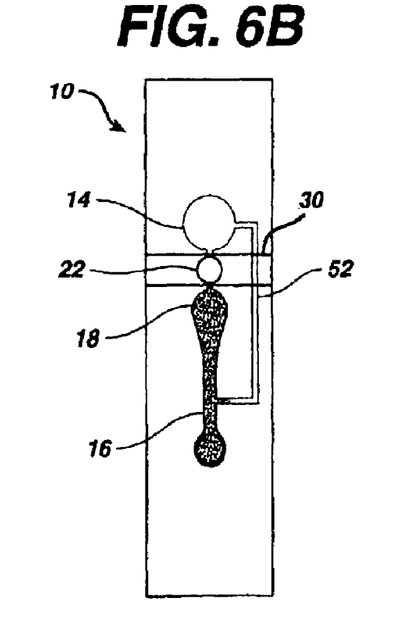

FIG. 6B depicts the situation after the bladder is decompressed. The resulting reduced pressure in the inlet channel 16 draws the sample initially into the measurement area 18. When the sample reaches stop junction 22, the sample encounters a back pressure that causes it to stop and causes additional sample to be drawn into the bypass channel.

Figure 6C:
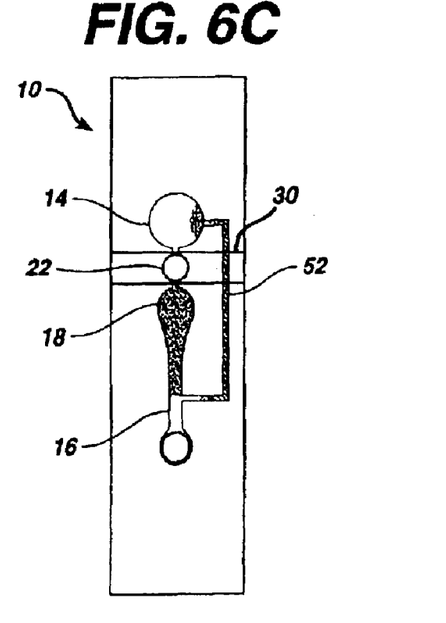

FIG. 6C depicts the situation when a reading is taken. Sample is isolated and at rest in measurement area 18. Excess sample and/or air has been drawn into bypass channel 52.

The bypass channel of FIG. 6 provides an important improvement over the operation of the "basic" strip of FIGS. 1–3. In the basic strip, stop junction 22 stops the flow of sample after it fills measurement area 18. As was discussed earlier, it is important to stop the flow in order to facilitate rouleaux formation. As was also discussed earlier, the stop junction accomplishes the flow stoppage as a result of surface tension acting on the meniscus at the leading edge of the fluid at an abrupt change in cross section of the flow channel. In the basic strip, the pressure on the bladder side of the stop junction remains below atmospheric pressure while the pressure on the sample side remains open to atmosphere. Thus, there is an ambient pressure imbalance on the two sides. The greater the imbalance, the greater the risk that the stop junction will leak and that sample will flow through the stop junction, interfering with rouleaux formation, and, consequently, providing inaccurate values of PT.

Bypass channel 52 minimizes that risk. The reduced pressure on the bladder side of the stop junction draws sample into the bypass channel (FIGS. 6B, 6C) until the ambient pressure is equalized at atmospheric pressure on both sides of the stop junction. Note that the (reduced) pressure on the bladder side is relatively uncontrolled. The bypass channel 52, by enabling the pressures on the two sides of the stop junction to equilibrate, permits the use of larger bladders that have greater suction. Larger bladders, in turn, provide more reliable operation of the system.

Figure 7:
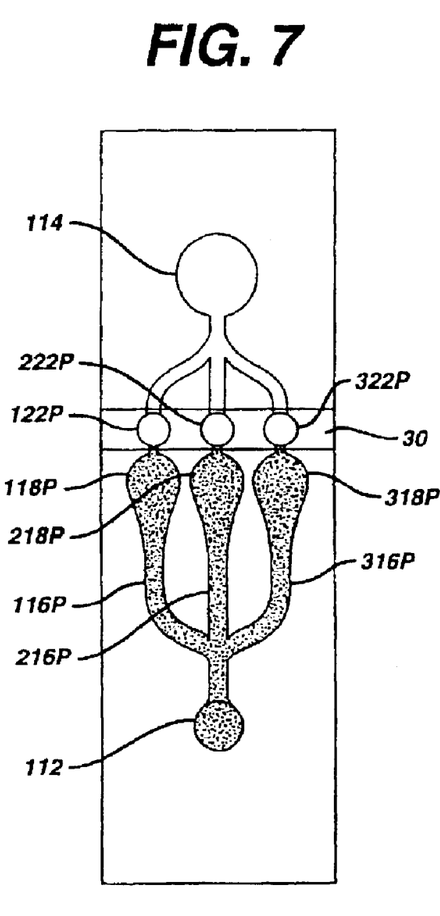
FIG. 7 is a schematic of a device having multiple measurement areas in parallel, multiple stop junctions in parallel, and a single bladder.

FIG. 7 depicts an embodiment of the present invention in which there are multiple (three are shown) measurement areas "in parallel". That is to say that the channels 116P, 216P, and 316P fill substantially simultaneously (assuming they have the same dimensions). The situation depicted in FIG. 7, with channels and measurement areas filled with blood, is achieved, as discussed above, by applying sample to sample port 112 while bladder 114 is compressed, then releasing bladder 114. As discussed above, the first step is to apply sample to sample well 112 while bladder 114 is compressed. The second step is to release the bladder. Sample flows to measurement areas 118P, 218P, and 318P, and flow stops when sample reaches stop junctions, 122P, 222P, and 322P, respectively. The optional second and third measurement areas may contain, for example, reagents that neutralize the presence of interferents (such as heparin) in the blood, or that provide a built-in control on the PT measurement, or that measure another blood parameter (such as APPT).

Figure 8:
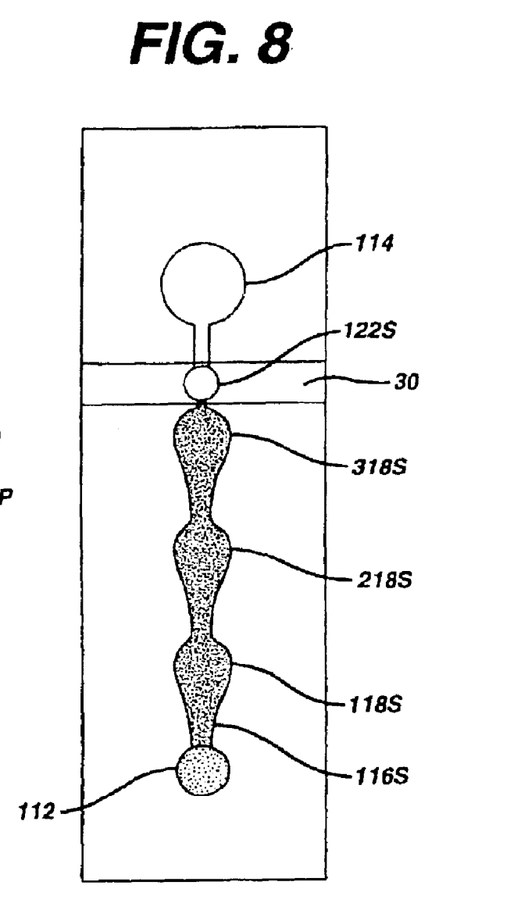
FIG. 8 is a schematic of a device having multiple measurement areas in series, with a single stop junction, a single bladder, and a filter over the sample port.

FIG. 8 is a schematic illustration of an embodiment in which multiple measurement areas are "in series", meaning that they fill sequentially. In this embodiment, measurement areas 118S, 218S, and 318S fill sequentially, through a single channel 116S, until the sample reaches stop junction 122S. A potential drawback of this design is that sample passing from one measurement area to the next may carry over reagent.

Figure 9:
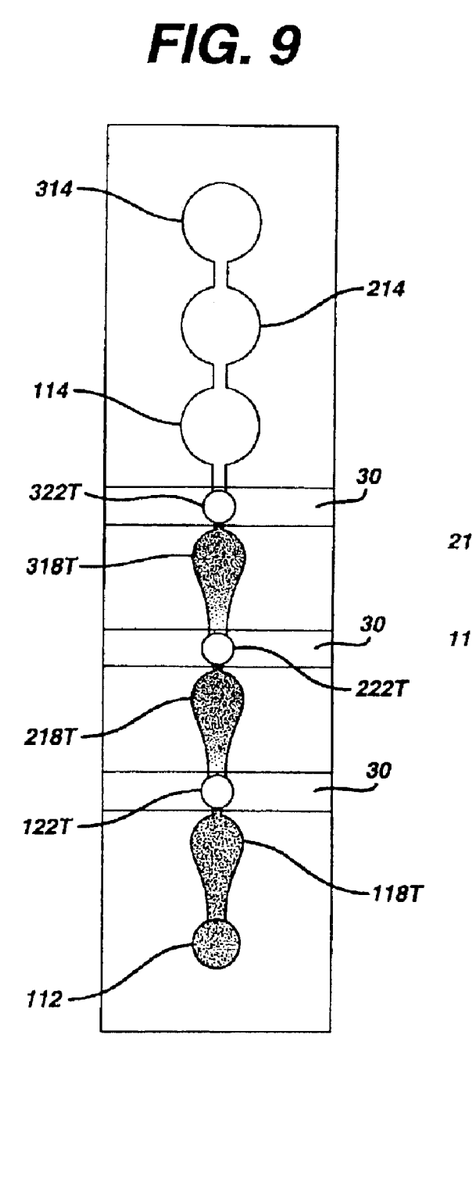
FIG. 9 is a schematic of a device having multiple measurement areas and multiple stop junctions arranged in an alternating series, as well as multiple bladders.

FIG. 9 is a schematic of another embodiment of a device that is adapted for multiple sequential tests. In that embodiment stop junctions 122T, 222T, and 322T permit a user to control the timing of sequential filling of measurement areas 118T, 218T, and 318T. In operation, bladders 114, 214, and 314 are all compressed before a blood sample is applied to sample well 112. Bladder 114 is then released to draw blood into measurement area 118T to stop junction 122T. At a selected later time, bladder 214 is released to permit blood to break through stop junction 122T and enter measurement area 218T to stop junction 222T. Finally, when the user wishes to use measurement area 318T, bladder 314 is decompressed, permitting sample to break through stop function 222T and flow to stop junction 322T. The device of FIG. 9 must be carefully formed, since the force drawing sample into the device—caused by decompressing a bladder—must be balanced against the opposing force—exerted by a stop junction. If the drawing force is too great, a stop junction may prematurely permit sample to pass; if it's too small, it will not draw the sample through a stop junction, when that is intended.

Figure 10:
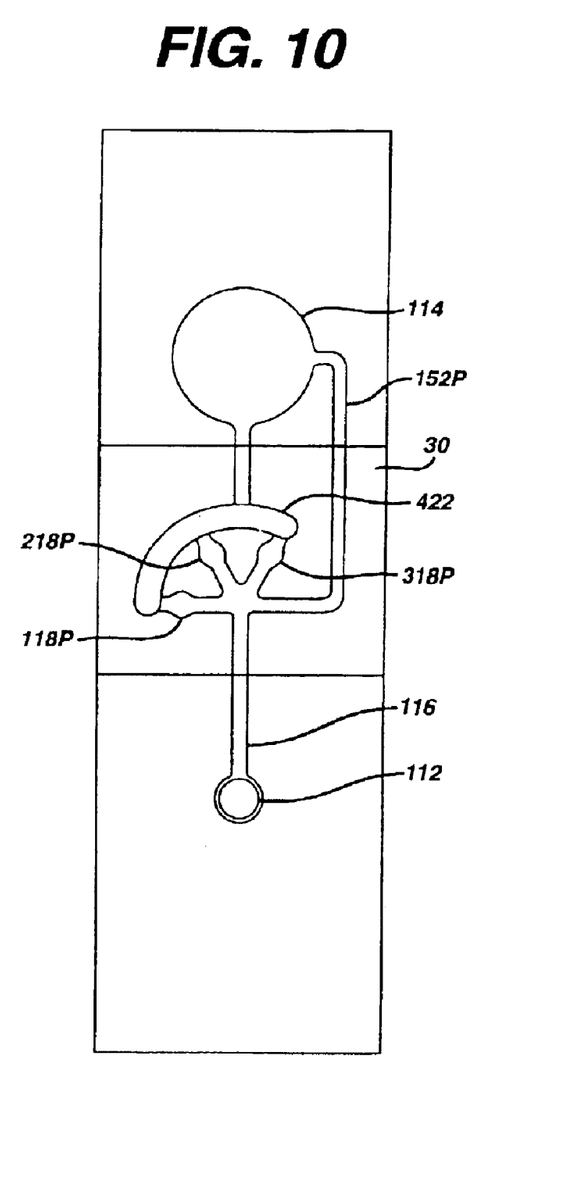
FIG. 10 is a schematic of a device that includes multiple measurement areas in parallel, a single bladder, and a single bypass channel.

FIG. 10 depicts a preferred embodiment of the present device. It is a parallel multi-channel device that includes bypass channel 152P Bypass channel 152P serves a purpose in this device that is analogous to that served by bypass channel 52 in the device of FIG. 6, which was described above. Measurement area 118P contains thromboplastin. Preferably, measurement areas 218P and 318P contain controls, more preferably, the controls described below.

Area 218P contains thromboplastin, bovine eluate, and recombinant Factor VIIa. The composition is selected to normalize the clotting time of a blood sample by counteracting the effect of an anticoagulant, such as warfarin. Measurement area 318P contains thromboplastin and bovine eluate alone, to partially overcome the effect of an anticoagulent. Thus, 3 measurements are made on the strip. PT time of the sample, the measurement of primary interest, is measured on area 118P. However, that measurement is validated only when measurements on areas 218P and 318P yield results within a predetermined range.

If either or both of these control measurements are outside the range, then a retest is indicated. Extended stop junction 422 stops flow in all three measurement areas.

Figure 11:
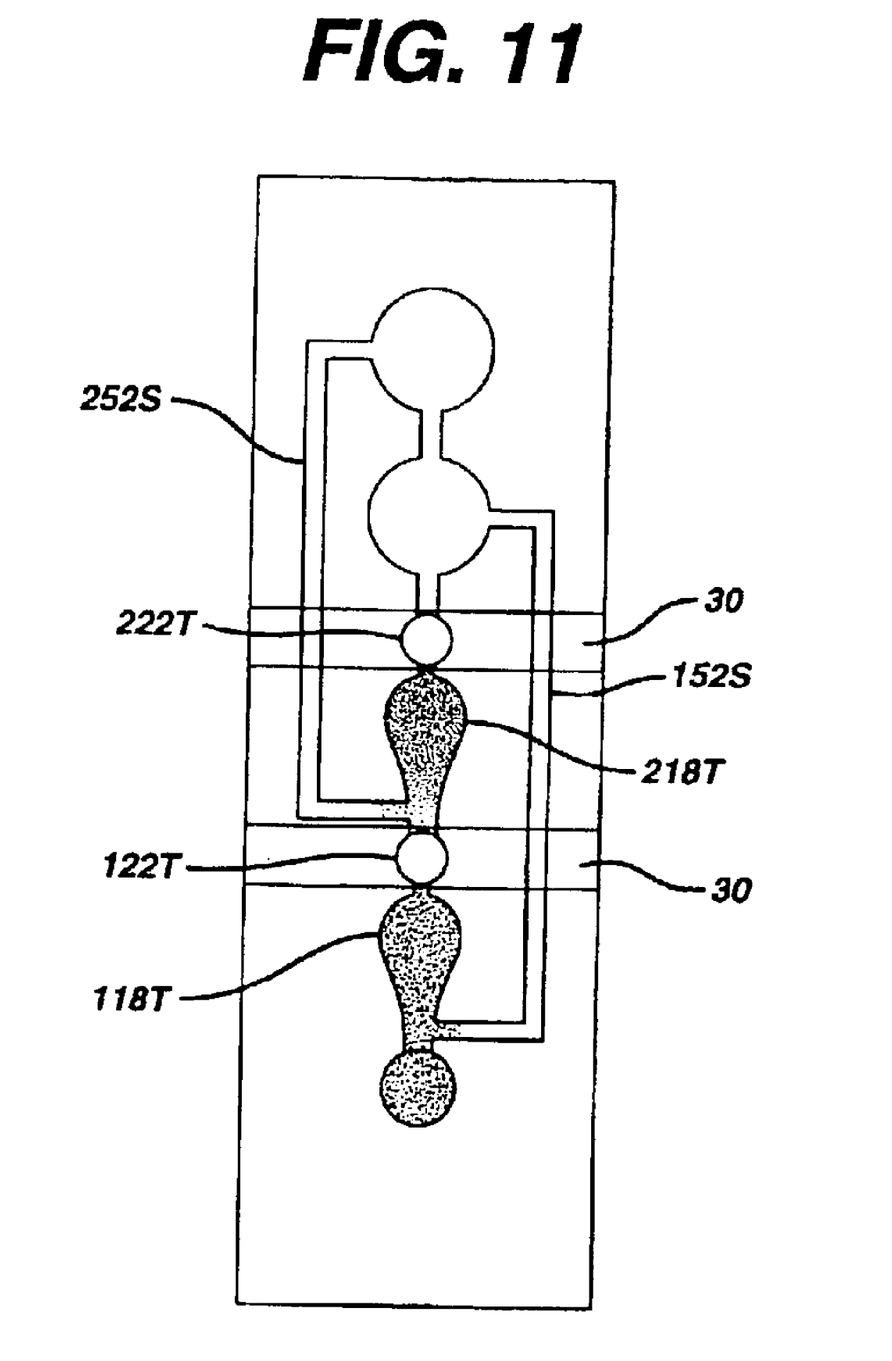
FIG. 11 is a schematic of a device having multiple measurement areas in series, multiple stop junctions in series, multiple bladders in series, and multiple bypass channels.

FIG. 11 depicts a device that includes bypass channels 152S and 252S to permit timed filling of measurement areas 118T and 218T. Operation of the device of FIG. 11 is analogous to that of the device of FIG. 9, described above, with the following exception. First bypass channel 152S has a region in which a reagent that causes clotting, such as thromboplastin, is coated. As a first measurement is made in reagent area 118T, a clot forms in blood that had been drawn into bypass channel 152S. Thus, when the second bladder is decompressed, blood is blocked from being drawn through bypass 152S and instead is drawn though stop junction 122T to measurement area 218T and bypass channel 252S.

Figure 12:
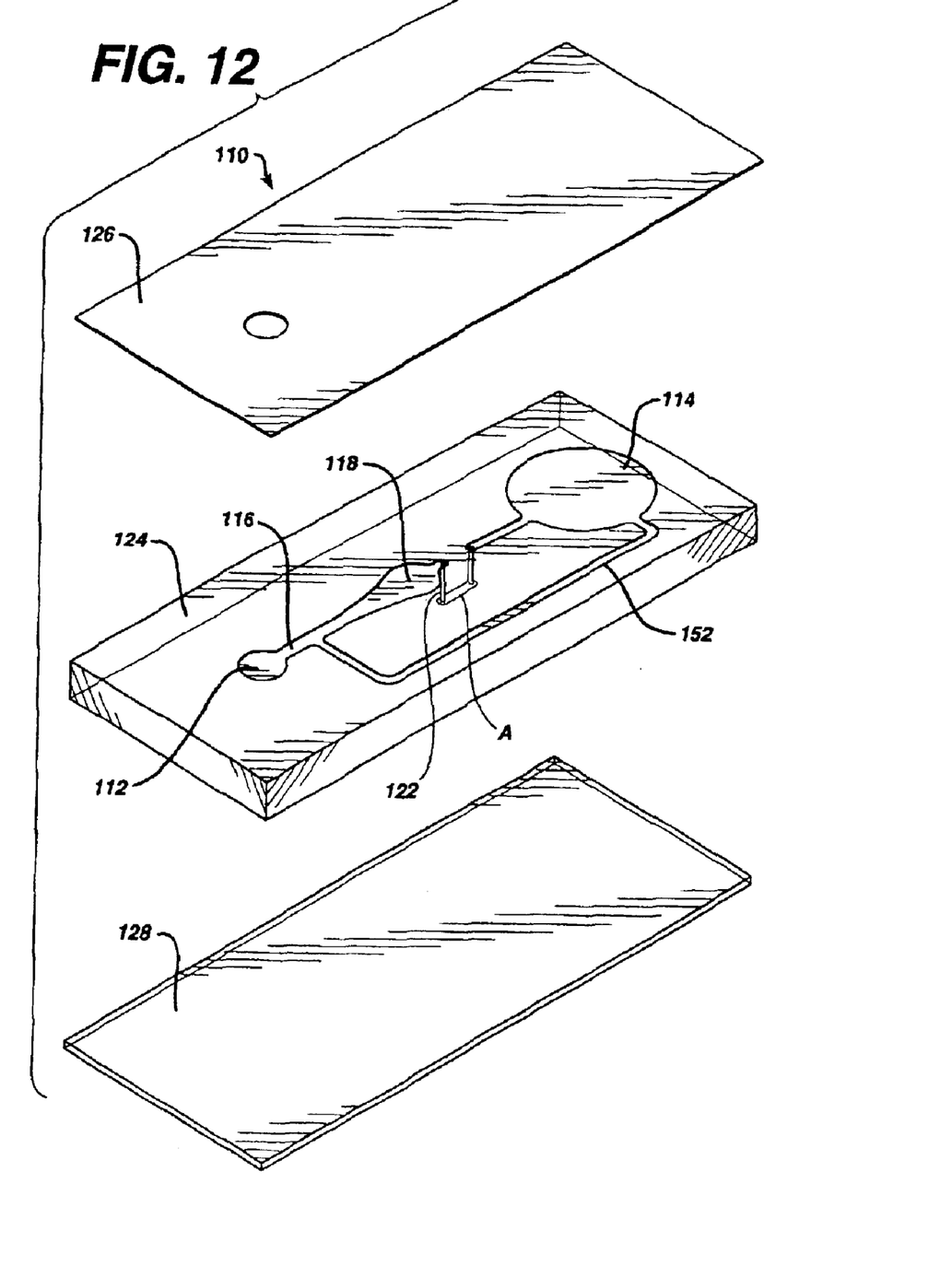
FIG. 12 is an exploded view of an injection-molded device of this invention.
Figure 13:
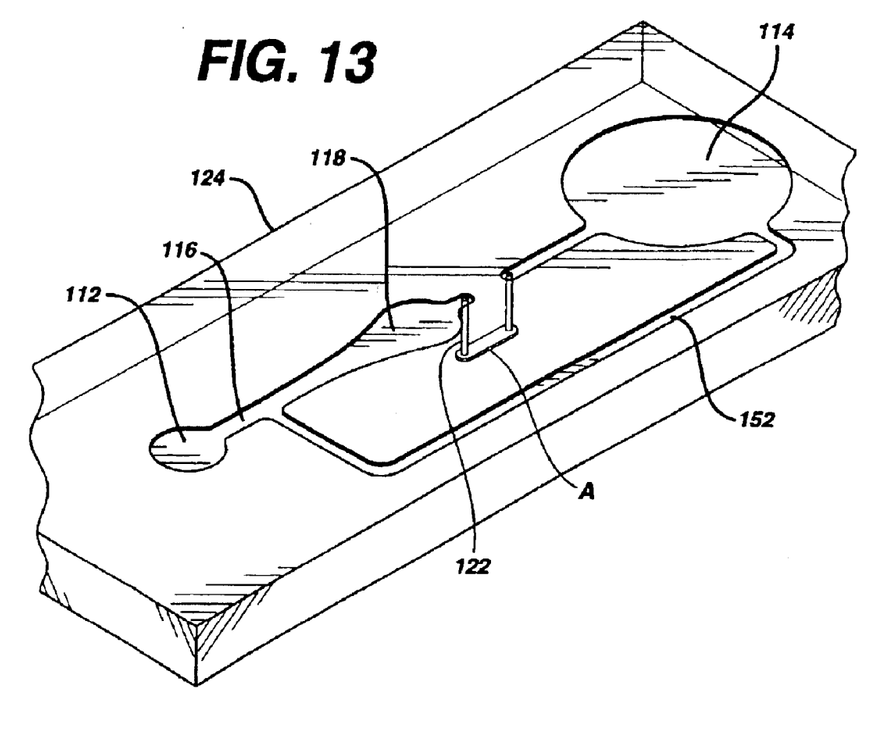
FIG. 13 is a perspective view of the device of FIG. 12.

All the previous figures depict the device of this invention as a laminated strip structure; however, the device could also be an injection-molded structure of the type shown in FIGS. 12 and 13. FIG. 12 is an exploded view of an injection-molded device 110, including top layer 126 and bottom layer 128 sandwiching intermediate layer 124. The intermediate layer has depressions in its top surface that form sample port 112, channel 116, measurement area 118, and optional bypass channel 152. Stop junction 122 passes through the thickness of intermediate layer 124. Sample flow stops at the interface between stop junction 122 and channel A, which is formed by a depression in the bottom surface. Thus, the sample flows from sample port 112 through channel 116 to measurement area 118 into stop junction 122.

The principle of operation of the injection molded device is the same as described above. It provides greater flexibility in the design of the stop junction, as well as the other elements of the device, because a wide range of channel cross sections are feasible. The molded structure also provides more rigidity, although it is substantially more costly.

The following examples demonstrate the present invention in its various embodiments, but are not intended to be in any way limiting.

EXAMPLE 1

A strip of this invention is made by first passing a double-sided adhesive tape (RX 675SLT, available from Scapa Tapes, Windsor, Conn.) sandwiched between two release liners into a laminating and rotary die-cutting converting system. The pattern shown in FIG. 6, with the exception of the stop junction, is cut through the top release liner and tape, but not through the bottom release liner, which is then removed as waste, along with the cutouts from the tape. Polyester film treated to be hydrophilic (3M9962, available from 3M, St. Paul, Minn.) is laminated to the exposed bottom side of the tape. Reagent (thromboplastin, available from Ortho Clinical Diagnostics, Raritan, N.J.) is then printed onto the reagent area (18) of the polyester film by bubble jet printing, using printing heads 51612A, from Hewlett Packard, Corvallis, Oreg. A sample port is cut in untreated polyester film (AR1235, available from Adhesives Research, Glen Rock, Pa.) and then laminated, in register, to the top of the double-sided tape (after removing the release layer). A die then cuts the stop junction through the three layers of the sandwich. Finally, strips of single-sided adhesive tape (MSX4841, available from 3M, St. Paul, Minn.) are applied to the outside of the polyester layers to seal the stop junction.

EXAMPLE 2

A procedure that is similar to the one described in Example 1 is followed to make a strip of the type depicted in FIG. 10. Reagent that is bubble-jet printed onto areas 118P, 218P, and 318P is, respectively, thromboplastin; thromboplastin, bovine eluate, and recombinant Factor VIIa; and thromboplastin and bovine eluate alone. The bovine eluate (plasma barium citrate bovine eluate) is available from Haemotologic Technologies, Burlington, Vt.; and recombinant Factor VIIa from American Diagnostica, Greenwich, Conn.

Measurements made on a whole blood sample using the strip of this Example yield a curve of the type shown in FIG. 5 for each of the measurement areas. The data from the curves for the controls (measurement areas 218P and 318P) are used to qualify the data from the curve for measurement area 118P. As a result, the PT time can be determined more reliably than can be done with a strip having a single measurement area.

EXAMPLE 3

The device of FIGS. 12 and 13 is formed by sandwiching middle layer 124 between top layer 126 and bottom layer 128. The middle and bottom layers are injection molded polycarbonate (Lexan*121) and have thicknesses of 6.3 mm and 1.5 mm, respectively. Top layer 126 is made by die cutting 0.18 mm Lexan*8010 sheet. The elements are ultrasonically welded after the reagent of Example 1 is applied to reagent area 118. The Lexan*material is available from General Electric, Pittsfield, Mass.

The invention having been fully described, it will be apparent to one of ordinary skill in the art that many modifications and changes may be made to it without departing from the spirit and scope of the present invention.

We claim:

1. An optical meter that can determine when sample has been applied to the surface of a test strip inserted into it, said meter comprising:
    (a) means for collecting reflectance data from a region of said meter occupied by a sample application location of said test strip when present in said meter, wherein said means comprises:
        (i) a light source for irradiating said region of said meter; and
        (ii) a detector for detecting reflected light from said region of said meter;
    (b) means for comparing said reflectance data to a reference value to obtain a sample present signal; and
    (c) means for depressing a bladder of said test strip in response to said sample present signal.
2. The optical meter according to claim 1, wherein said meter further comprises said test strip.
3. The optical meter according to claim 1, wherein said test strip is present in said meter.
4. The optical meter according to claim 1, wherein said test strip is a non-porous test strip.
5. The optical meter according to claim 1, wherein said light source is a source of visible light.
6. The optical meter according to claim 5, wherein said light has a wavelength ranging from about 550 nm to 590 nm.

* * * * *